United States Patent [19]

Cheng

[11] Patent Number: 4,517,182

[45] Date of Patent: May 14, 1985

[54] 3-(HALOETHYL)-4-OXOPYRAZOLO-[5,1-D]-1,2,3,5-TETRAZINE-8-CARBOXAMIDE COMPOSITION

[75] Inventor: Chia-Chung Cheng, Leawood, Kans.

[73] Assignee: Warner-Lambert Company, Morris Plains, N.J.

[21] Appl. No.: 594,919

[22] Filed: Apr. 3, 1984

Related U.S. Application Data

[63] Continuation-in-part of Ser. No. 497,587, May 24, 1983.

[51] Int. Cl.³ .................. A61K 31/395; A61K 31/55; C07D 257/08
[52] U.S. Cl. .................................. 514/413; 544/179
[58] Field of Search ........................ 544/179; 424/244

[56] References Cited

PUBLICATIONS

Ege et al., Chemical Abstracts, vol. 95, entry 7353n, (1981).

Ege et al., Tetrahedron Letters, No. 44, pp. 4253–4256, (1979).

Primary Examiner—John M. Ford
Attorney, Agent, or Firm—Krass and Young

[57] ABSTRACT

The title compounds are provided as well as a method for their production, pharmaceutical compositions comprising the compounds, and a method of treatment using the compounds in dosage form. Compounds of the invention have pharmacological properties and are useful antimicrobial agents and antileukemic agents.

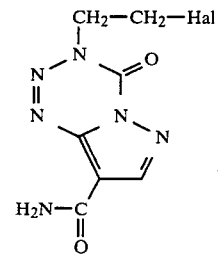

4 Claims, No Drawings

3-(HALOETHYL)-4-OXOPYRAZOLO-[5,1-D]-1,2,3,5-TETRAZINE-8-CARBOXAMIDE COMPOSITION

REFERENCE TO RELATED APPLICATION

This is a continuation-in-part of copending patent application Ser. No. 497,587, filed May 24, 1983.

TECHNICAL FIELD

The invention relates to novel 3-(2-haloethyl)-4-oxopyrazolo-[5,1,-d]-1,2,3,5-tetrazine-8-carboxamide compounds, to a method for their production, to pharmaceutical compositions comprising the compounds, and to methods of treatment using the compounds in dosage form. The compounds of the invention have pharmacological properties and are useful antimicrobial agents and antileukemic agents.

BACKGROUND OF THE INVENTION

Azolo-[5,1-d]-[1,2,3,5]-tetrazin-4-ones are known from Tetrahedron Letters No. 44, pp. 4253-4256, Pergamon Press Ltd. 1979 and Chemical Abstracts, 95, 698, 1981. The title compounds are unknown in the prior art.

SUMMARY OF THE INVENTION

The invention in one aspect relates to 3-(2-haloethyl)-4-oxopyrazolo[5,1-d]-1,2,3,5-tetrazine-8-carboxamide compounds having the structural formula:

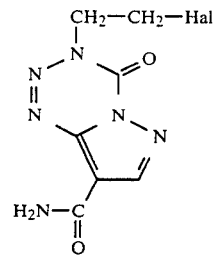

where Hal is a halogen. According to the invention, the halogen may be chloro, bromo, iodo or fluoro, preferably chloro.

PROCESS FOR PREPARING THE COMPOUNDS

The invention in another aspect comprises a process for preparing the title compounds having the above structural formula, which comprises reacting 3-diazapyrazole-4-carboxamide and a haloethylisocyanate having the structural formula Hal—$CH_2$—$CH_2$—N=C=O under cyclizing conditions and isolating the product where Hal has the above meaning. The reaction is suitably carried out in a dry inert organic solvent such as ethyl acetate, with mixing at room temperature for a short period and then at higher temperature, for example, at about 50 to about 60 degrees celsius. Heating is continued until the reaction is complete at which time the mixture becomes a solution. Purification of compounds or products obtained by the method of the invention is accomplished in any suitable way, preferably by column chromatography or crystallization. The starting materials either are known or can be prepared from known materials by procedures described herein starting from ethoxymethylene malonitrile (I) and hydrazine (II). The procedure is illustrated as follows:

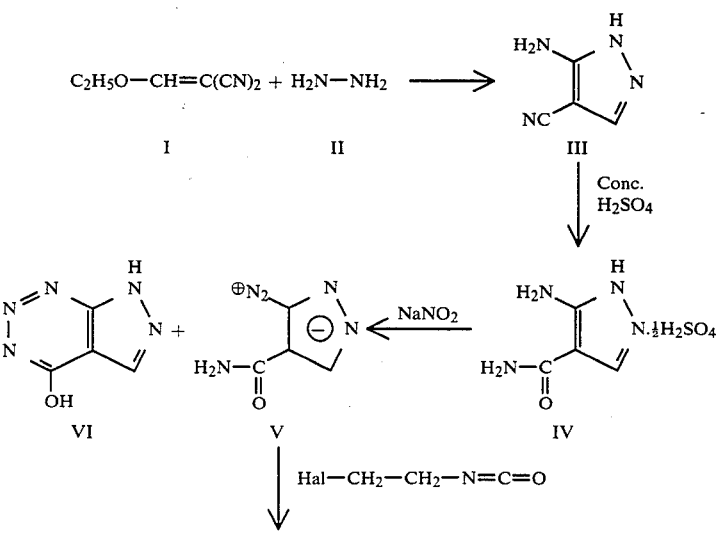

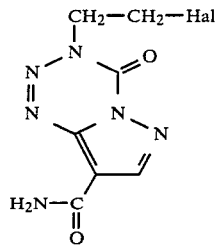

PHYSICAL AND PHARMACOLOGICAL PROPERTIES OF THE COMPOUNDS

The compounds of the invention typically are light stable, have antimicrobial properties and leukemia-inhibiting properties, and are useful as pharmacological agents in dosage form for the treatment of microbial infections or leukemia in warm-blooded animals. They may also be utilized as antiseptic agents, such as for use as an active antimicrobial ingredient in a composition for the sterilization of laboratory glassware, etc. The activity of test compounds is established by test protocols described below.

TEST PROTOCOLS

1. In vitro

One test protocol is the in vitro antibacterial/antifungal (ABF) test. Compounds are tested for antimicrobial activity in an agar-disk diffusion assay, a standard microbiological technique for testing antibiotics. After incubation of each culture with a test compound, a zone of inhibition is determined. The zone diameter (mm) of active compounds ranges from a minimum of 14 mm to as high as 18 mm, with a greater diameter reflecting higher activity. For convenience, values are reported for three species, *Alcaligenes viscolactis, Kloeckera brevis,* and *Penicillium avellaneum*.

2. In vivo

Another test protocol is the in vivo L1210 leukemia test. This assay is carried out with male $DC_2F_1$ mice (six per treatment group) that weigh 22–24 grams at first treatment. L1210 leukemia cells are harvested from the peritoneal ascites fluid of a leukemic male $DBA_2$ mouse and diluted with sterile 0.9% saline containing 2.1% W/V bovine serum albumin, 200U/ml penicillin, and 0.3 mg/ml streptomycin. The cells are counted with a Coulter® counter. The mice are randomized, inoculated with $10^4$ L1210 cells (0.5 ml, i.p.) and rerandomized to treatment or control groups on day zero. The test compound is dissolved in 10% aqueous dimethylsulfoxide. Treatment groups are injected i.p. with 0.5 ml of freshly made DMSO solutions of the test compound once daily on days 3–7. Control mice are treated with 0.5 ml 10% dimethylsulfoxide. All mice are weighed on days 3 and 7 and all dying mice are autopsied to confirm the presence of advanced leukemia. A %T/C value [T/C computed as (median lifespan of the treated group/median lifespan of the control group)] greater than 125 is considered as showing significant activity. The results for compounds and compositions of the invention exemplified by a preferred compound of the invention, 3-(2-chloroethyl)-4-oxopyrazolo-[5,1-d]-1,2,3,5-tetrazine-8-carboxamide, also known as pyraoncozine, are presented in Table 1 and Table 2.

TABLE 1

| Antimicrobial activity of Pyraoncozine | |
|---|---|
| Microorganism | Inhibition Zone Diameter mm (concentration mg/ml) |
| *Alcaligenes viscolactis* | 24(3.0) |
| *Kloeckera brevis* | 15(0.5) |
| *Penicillium avellaneum* | 14(3.0) |

TABLE 2

| | L1210 Activity* | | | |
|---|---|---|---|---|
| Dose (mg/kg/inj.) | D Weight** (g) | Median Lifespan | % T/C | 21-Day Survivors |
| Control | +1.0 | 10.4 | — | 0/20 |
| 40 | −4.3 | 21.5 | 207 | 6/6 |
| 20 | −1.8 | 20.7 | 199 | 0/6 |
| 10 | −0.1 | 13.2 | 127 | 0/6 |
| 5 | +0.7 | 12.2 | 117 | 0/6 |
| 2.5 | +1.7 | 11.7 | 112 | 0/6 |

*L1210 - $10^4$ cells, i.p., day zero
Treatment i.p., days 3–7.
*Dwt = (mean, day 3)–(mean, day 7).

The invention in its composition aspect relates to a pharmaceutical composition for treating microbial infection comprising a compound having the above structural formula in combination with a pharmaceutically acceptable carrier.

The invention in another composition aspect relates to a pharmaceutical composition for treating leukemia in a dosage form comprising a compound of the invention having the above structural formula, preferably 3-(2-chloroethyl)-4-oxopyrazolo-[5,1-d]-1,2,3,5-tetrazine-8-carboxamide, in combination with a pharmaceutically acceptable carrier.

The invention in a method aspect relates to a method for treating microbial infection in a mammal which comprises administering a dosage form containing a microbe-inhibiting amount of compound having the above structural formula, in combination with a pharmaceutically acceptable carrier, to a mammal in need thereof.

The invention in another method aspect relates to a method for treating leukemia in a mammal which comprises administering a dosage form containing a leukemia-inhibiting amount of compound of the invention having the above structural formula, preferably 3-(2-chloroethyl)-4-oxopyrazolo-[5,1-d]-1,2,3,5-tetrazine-8-carboxamide, in combination with a pharmaceutically acceptable carrier, to a mammal in need thereof.

PREPARATION OF PHARMACEUTICAL COMPOSITIONS

When being utilized as pharmacological agents, the compounds of the invention can be prepared and administered in a wide variety of topical, oral and parenteral dosage forms. It will be clear to those skilled in the art that the following dosage forms may comprise as the active component, one or more compounds of the above fomula.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well-known procedures. See for example Remington's Pharmaceutical Sciences, Chapter 43, 14th Ed., Mack Publishing Co., Easton, Pennsylvania 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents the compounds utilized in the pharmaceutical method of this invention are administered at the initial dosage of about 0.1 mg to about 100 mg per kilogram. A dose range of about 4.0 mg to about 40 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional medium or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specifications for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 4.0 mg/kg to 40 mg/kg.

The invention and the best mode of practicing the same are illustrated by the following examples of preferred embodiments of selected compounds and their preparation.

EXAMPLE 1

3-Amino-4-cyanopyrazole (III)

This compound was reported by R. K. Robins, J. Am. Chem. Soc., 78: 784 (1956). Following is a modified procedure.

To 74 g of 64% hydrazine (II) in water (1.5 mole) was added portionwise 100 g (0.82 mole) of ethoxymethylenemalononitrile (I) with stirring. An exothermic reaction occurred during the addition. After the addition was complete, the brown solution was heated in a water bath for 4 hours. The resulting solution was placed in a refrigerator overnight. Light brown crystals, which formed from the reaction mixture, was collected by filtration, washed with cold water and ether, and dried to give 63 g (71% yield) of III as light brown crystals, m.p. 169–170 degrees C. It was used for the next reaction without further purification.

EXAMPLE 2

3-Amino-4-pyrazolecarboxamide Hemisulfate (IV)

This compound was reported by R. K. Robins, J. Am. Chem. Soc., 78: 784 (1956). Following is a modified procedure.

To 180 ml of concentrated sulfuric acid cooled in an ice bath was added portionwise, with stirring, 56 g (0.52 mole) of finely powdered III. The addition was at such a rate that the temperature of the stirred reaction mixture remained at or below 20 degrees C. Total addition time: 2.5 hrs.

After the addition was complete, the reaction mixture, which still contained some solids, was stirred at 10–20 degrees C. for 30 minutes, then at room temperature for 4 hrs. The resulting dark brown solution was slowly poured, with vigorous stirring, onto 1 kg of crushed ice in a large beaker. Light brown solid product separated immediately. The resulting reaction mixture was stored in a refrigerator overnight. The solid was then collected by filtration, washed successively with water, a small amount of ethanol, and ether. It was then dried at 50 degrees C. under reduced pressure for 18 hrs to give 102 g (100% yield) of IV as light brown solids, m.p. 217–218 degrees C. dec. It was used for the next reaction without further purification.

EXAMPLE 3

3-Diazapyrazole-4-carboxamide(3-Diazonium,-pyrazole-4-carboxamide hydroxide inner salt) (V) and 4-Hydroxypyrazolo[3,4-d]-v-triazine (VI)

These compounds were reported by C. C. Cheng, R. K. Robins, K. C. Cheng, and D. C. Lin, J. Pharm. Sci., 57:1044 (1968). Following is a modified procedure.

A stirred mixture of 18 g (0.103 mole) of finely powdered IV in 180 ml of water was cooled at 0–5 degrees. To this suspension was added, with vigorous stirring, 8 g (0.116 mole) of sodium nitrite. The mixture was stirred at 0–5 degrees for 20 minutes and filtered through a sintered glass funnel. The solid was thoroughly washed with 2×20 ml of cold water, 20 ml of ethanol, and 50 ml of ether. Agitation of the solid during washing is very important in this operation. The remaining light brown crystalline solid was then carefully transferred to a crystalline dish and dried at room temperature in vacuo to give 6.9 g (49% yield) of V. Its IR showed a characteristic triple bond absorption peak at 2235 cm$^{-1}$. The product decomposed in a melting point tube without melting on slow heating, but on rapid heating, it decomposed violently with a sharp sound at ca. 160 degrees C. Care, therefore, should be exercised for the handling of this compound. Rapid, repeated scratching of the dried powder with a spatula may cause its rapid decomposition.

From the filtrate there was obtained, on standing, 4.2 g (30% yield) of the triazine VI as light yellow shining platelets. This compound, on slow heating, did not melt below 300 degrees C. and, on rapid heating, decomposed with a muffled sound at ca. 170 degrees C. Unlike compound V, its IR did not show the triple bond absorption.

EXAMPLE 4

3-(2-Chloroethyl)-4-oxopyrazolo[5,1-d]-1,2,3,5-tetrazine-8-carboxamide (Pyraoncozine)

(a) To a mechanically stirred suspension of 2 g (0.0146 mole) of finely powdered V in 420 ml of dry ethyl acetate (caution: do not powder compound V alone, powder it in the ethyl acetate suspension) at room temperature was added 10.5 g (0.1 mole) of 2-chloroethylisocyanate. The mixture was stirred at room temperature in the absence of moisture for 30 min, then heated at 50–60 degrees C. with continuous stirring for 72 hrs. At the end of the period the suspension became a solution. A small amount of brown impurity was removed by filtration and the filtrate concentrated under reduced pressure at room temperature to 100 ml. The resulting light yellow solid was collected by filtration, washed with 200 ml of ether and dried at room temperature in vacuo to give 1.6 g (45% yield) of the desired product in analytically pure form, m.p. 193-194 degrees C. dec. From the filtrate there was obtained, on further concentration, 0.9 g of product, m.p. 167-169 degrees C. dec. Its IR spectrum was comparable to that of the first crop but tlc (EtOAc) indicated the presence of two spots. The desired product, pyraoncozine, can be separated from its isomer by means of column chromatography using ethyl acetate as the eluant through a silica gel column. The purified product was isolated as white fluffy needles, melted sharply at 200 degrees C. dec.

Anal. for $C_7H_7ClN_6O_2 \cdot \frac{1}{2}H_2O$: C, 33.41; H, 3.20; N, 33.40. Found: C, 33.10; H, 2.98; N, 33.20

Mass spectrum of the product: 242 (M+), 226 (M+-$NH_2$), 193 (M+-$CH_2Cl$), 137 (M+-$ClCH_2CH_2N_3$). $\lambda$ max $CHCl_3$ 314 nm ($\epsilon$ 8550).

The product is stable in chloroform solution but unstable in methanol. The UV absorption maximum of the compound in methanol, on standing, gradually shifted from 310 nm to 256 nm.

(b) By the same procedure, but replacing the chloroethylisocyanate with a different, but requivalent amount of, haloethylisocyanate such as 2-bromoethylisocyanate, 2-fluoroethylisocyanate, or 2-iodoethylisocyanate, there are obtained:

3-(2-bromoethyl)-4-oxopyrazolo-[5,1-d]-1,2,3,5-tetrazine-8-carboxamide, 3-(2-fluoroethyl)-4-oxopyrazolo-[5,1-d]-1,2,3,5-tetrazine-8-carboxamide, or 3-(2-iodoethyl)-4-oxopyrazolo-[5,1-d]-1,2,3,5-tetrazine-8-carboxamide.

Having thus described our invention, what we claim and desire by Letters Patent to secure are the following:

1. A pharmaceutical composition for treating microbial infection in a dosage form comprising a microbe-inhibiting amount of a 3-(2 haloethyl)-4-oxopyrazolo[5,1-d]-1,2,3,5-tetrazine-8-carboxamide compound having the structural formula where Hal is a halogen, in combination with a pharmaceutically acceptable carrier.

2. A pharmaceutical composition according to claim 1 where the dosage form contains 3-(2-chloroethyl)-4-oxopyrazolo-[5,1-d]-1,2,3,5-tetrazine-8-carboxamide.

3. A method for treating microbial infection in a mammal which comprises administering a dosage form containing a microbe-inhibiting amount of compound having the structural formula according to claim 1, in combination with a pharmaceutically acceptable carrier, to a mammal in need thereof.

4. A method for treating microbial infection in a mammal which comprises administering a dosage form containing a microbe-inhibiting amount of chloroethyl compound having the structural formula according to claim 1, in combination with a pharmaceutically acceptable carrier, to a mammal in need thereof.

* * * * *